United States Patent [19]
Saab

[11] Patent Number: 5,499,973
[45] Date of Patent: Mar. 19, 1996

[54] VARIABLE STIFFNESS BALLOON DILATATION CATHETERS

[76] Inventor: Mark A. Saab, 396 Andover St., Lowell, Mass. 01852

[21] Appl. No.: 302,267

[22] Filed: Sep. 8, 1994

[51] Int. Cl.⁶ ................................................. A61M 29/00
[52] U.S. Cl. ...................... 604/96; 604/101; 604/264; 606/194; 128/658
[58] Field of Search ........................... 604/96, 101, 282, 604/264; 606/194; 128/658

[56] References Cited

U.S. PATENT DOCUMENTS

| | | |
|---|---|---|
| Re. 32,983 | 7/1989 | Levy . |
| 4,299,226 | 11/1981 | Banka . |
| 4,422,447 | 12/1983 | Schiff . |
| 4,540,404 | 9/1985 | Wolvek . |
| 4,576,772 | 3/1986 | Carpenter . |
| 4,581,017 | 4/1986 | Sahota . |
| 4,601,724 | 7/1986 | Hooven et al. . |
| 4,681,092 | 7/1987 | Cho et al. . |
| 4,681,564 | 7/1987 | Landreneau . |
| 4,739,768 | 4/1988 | Engelson . |
| 4,820,349 | 4/1989 | Saab . |
| 4,869,263 | 9/1989 | Segal et al. . |
| 4,976,690 | 12/1990 | Solar et al. . |
| 4,994,033 | 2/1991 | Shockey et al. . |
| 5,049,132 | 9/1991 | Shaffer et al. . |
| 5,085,649 | 2/1992 | Flynn . |
| 5,108,370 | 4/1992 | Walinsky . |
| 5,250,059 | 10/1993 | Andreas et al. . |
| 5,308,342 | 5/1994 | Sepetka et al. . |
| 5,411,477 | 5/1995 | Saab . |

Primary Examiner—C. Fred Rosenbaum
Assistant Examiner—Perry E. Van Over
Attorney, Agent, or Firm—Lappin & Kusmer

[57] ABSTRACT

A variable stiffness balloon dilatation catheter is disclosed in which one or more polymeric sleeves are heat-shrunk around portions of an inner tubular element so as to form stiffening bands that provide variable stiffness longitudinally along the catheter.

82 Claims, 2 Drawing Sheets

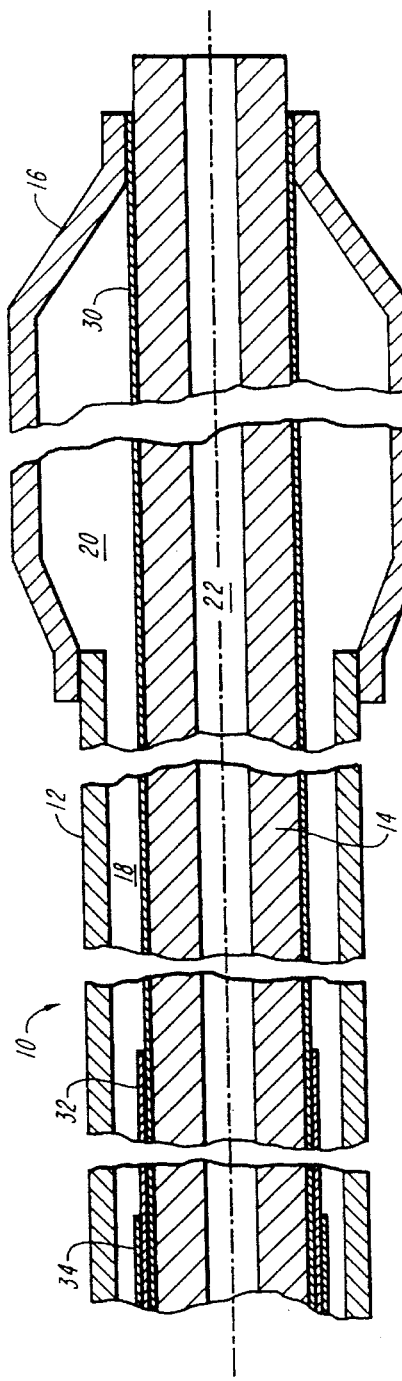
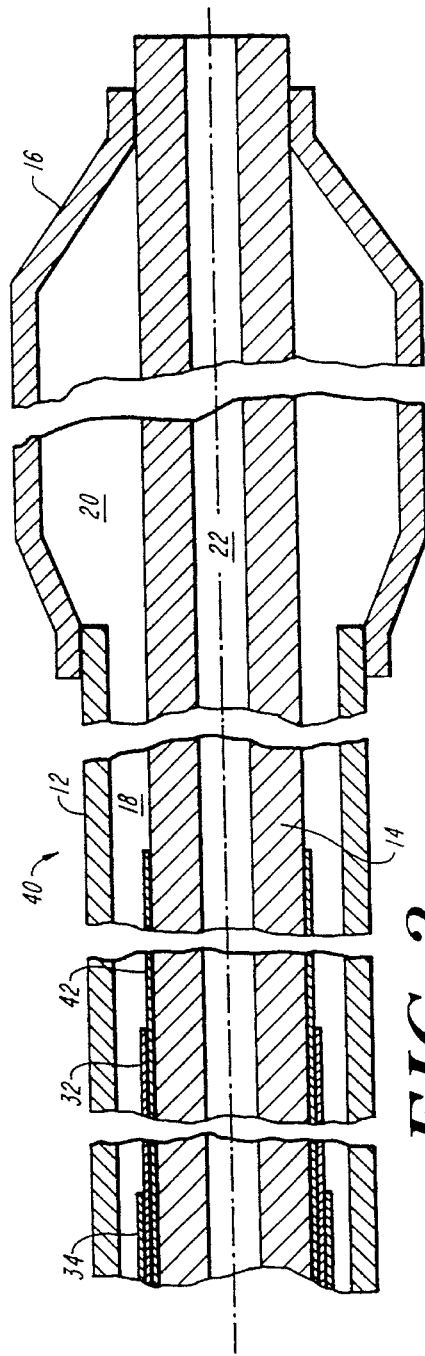

VARIABLE STIFFNESS BALLOON DILATATION CATHETERS

The present invention relates generally to balloon dilatation catheter apparatus having a variable stiffness catheter shaft prepared utilizing a fabrication technique that readily lends itself to a wide range of special purpose catheter applications.

BACKGROUND OF THE INVENTION

Balloon dilatation catheter apparatuses for a variety of medical applications, such as percutaneous transluminal coronary angioplasty (PTCA), are well known in the art. The use and construction of such balloon catheters is well known in the medical art, as generally described for example in U.S. Pat. Nos. Re. 32,983 (Levy) and 4,820,349 (Saab). Other patents generally showing the application of various types of balloon catheters include U.S. Pat. Nos. 4,540,404 (Wolvek), 4,422,447 (Schiff), and 4,681,092 (Cho, et al.).

It is also well known in the medical art to employ catheters having shafts formed with a plurality of lumens in instances where it is necessary or desirable to access the distal end of the catheter or a particular internal body location simultaneously through two or more physically separate passageways. For example, U.S. Pat. No. 4,576,772 (Carpenter) is directed to increasing the flexibility or articulatability of a catheter having a shaft formed with a plurality of lumens that provide distinct conduits for articulating wires, glass fiber bundles, irrigation, and vacuum means.

It is also known, as shown in U.S. Pat. Nos. 4,299,226 (Banka) and 4,869,263 (Segal et al.), to employ multi-lumen catheters with a balloon. The Banka patent shows a double-lumen catheter shaft of coaxial construction wherein the outer lumen carries saline solution to inflate a balloon, and an inner lumen, located coaxially inside the outer lumen, is adapted to receive a stylet or guide wire. In the Banka patent, the double-lumen dilatation catheter is designed to be coaxially contained within the single lumen of a larger diameter guide catheter. The Segal et al. patent shows a more complex dilatation catheter apparatus having five separate, non-coaxial lumens (FIGS. 1 and 2 of that patent) extending through the catheter, including a balloon inflation lumen 18, a distal lumen 17, a wire lumen 22, a pulmonary artery lumen 26, and a right ventricular lumen 28. Lumens 17 and 18 extend the entire length of the catheter from the proximal extremity to the distal extremity. Lumen 17 exists through the distal extremity 14b of the catheter. The distal extremity of lumen 18 is in communication with the interior of balloon 16 to permit inflation and deflation. Lumens 22, 26 and 28, on the other hand, only pass partly or completely through the larger diameter, proximal portion 14a of the catheter. The Segal et al. catheter apparatus is prepared by extrusion (col. 2, lines 53 and 54).

Multi-lumen catheters in conjunction with a balloon or inflatable element have also been adapted for a variety of special usages. U.S. Pat. Nos. 4,994,033 (Shockey et al.) and 5,049,132 (Shaffer et al.) are both directed to balloon catheters adapted for intravascular drug delivery. Both of these patents employ a similar concentric, coaxial, double balloon construction surrounding a central lumen. The larger, outer balloons in both cases include a set of apertures for the delivery of medication to surrounding tissue when the catheter is in place.

U.S. Pat. No. 4,681,564 (Landreneau) teaches another type of multi-lumen catheter in conjunction with a balloon element. In this patent, a first fluid passage is in communication with the balloon element so as to selectively inflate or deflate it; a second, separate fluid passage has outlet openings at its distal end for purposes of delivering medication or other treating fluid to the body space; and, a third, separate passage has drain openings communicating with the body space so as to drain excess fluids.

U.S. Pat. Nos. 4,581,017 (Sahota) and 5,108,370 (Walinsky) are both directed to perfusion balloon catheters designed to maintain blood flow through a blood vessel during a dilatation procedure, for example an angioplasty. In Sahota, a hollow, central shaft passes through the interior of the balloon element, and apertures in the side wall of the catheter shaft upstream and downstream from the balloon permit blood to flow into the shaft, past the balloon, and back into the blood vessel. A small, separate tube connected to the balloon is used to inflate and deflate the balloon. A generally similar balloon catheter construction is described in Walinsky.

For many balloon dilatation catheter applications, it is desirable to provide an elongated catheter shaft having varying degrees of stiffness along its length. For example, it is generally desirable to have a relatively stiff proximal shaft portion in order to transmit the necessary forces, particularly torque or axial forces, for advancing the catheter along a guide wire inside a body passageway for purposes of siting the balloon element at a selected internal location. At the same time, a more flexible "waist" or middle shaft portion can facilitate maneuvering the distal end of the catheter around turns and convolutions in the inner portions of the passageway. Various approaches to fabricating a workable variable stiffness balloon catheter have been described in the art.

U.S. Pat. No. 4,976,690 (Solar et al.) teaches one type of variable stiffness angioplasty catheter. In Solar et al., a "waist" portion, located between the balloon and the stiffer proximal end, is designed to have less stiffness and a correspondingly greater degree of flexibility. Such a catheter is intended to be utilized as part of a matched set, each having a different length of the less-stiff "waist" portion, to accommodate the needs of a particular patient (col. 2, lines 32–35). In one embodiment (FIGS. 2A and 2B), the less-stiff waist portion, 14 and 14' respectively, of the Solar et al. catheter is formed by extending the proximal neck of the balloon element, which is fabricated from a less-stiff material, to form a tubing section 30 that mates with and is bonded to a reduced-neck portion 27 at the distal end of the outer tube 25. In another embodiment (FIGS. 4A and 4B), the less-stiff waist portion 14 and 14' respectively, of the Solar et al. catheter is formed by necking down the wall thickness of outer tube 55. In still another embodiment (FIGS. 5A and 5B), "the variable stiffness of the waist portion 14, 14' is provided by varying the wall thickness and stiffness of the inner tube of the catheter," (col. 5, lines 57–59). In yet another embodiment of Solar et al. (FIGS. 6A and 6B), a double-lumen tubing construction is utilized in conjunction with the general technique of FIGS. 2A and 2B to obtain variable stiffness properties.

U.S. Pat. No. 5,085,649 (Flynn) teaches a very different approach to variable stiffness tubing. The Flynn tubing generally comprises an inner tubular layer of two co-tapered resins and a relatively hard, concentric outer shell. The hardness of the inner resin layer exceeds that of the outer resin layer, as does the hardness of the outer shell. In effect, this construction sandwiches a relatively softer, tapered center layer between harder inner and outer layers to obtain a torque-controlled tubing.

None of these prior art patents, which are incorporated herein by reference, however, is entirely satisfactory when applied to balloon dilatation catheters. The tapered-layer tubing of the Flynn patent would be difficult if not impossible to produce, especially for extremely long, very-thin-walled, small diameter catheter tubing required for such applications as PTCA catheters. In any event, because of the tapered construction, stiffness along the length of the Flynn tubing varies constantly and uniformly. Thus, the Flynn technique cannot be used to create discrete sections of tubing, each halving its own, substantially uniform stiffness, or to fabricate tubing having sharp disjunctions in stiffness along its length.

Although the Solar et al. patent is specifically directed to balloon catheters, it too has inherent limitations. First, the various Solar et al. techniques only provide for two sections having different degrees of stiffness along the catheter. For some applications, however, it is desirable to provide more than two different stiffnesses along the catheter. Second, for the embodiments of FIGS. 2A, 2B, 4A, 4B and 6A, 6B of Solar et al., the range of stiffness and related properties that can be achieved along the "waist" portion of the catheter is severely restricted because of the fact that the waist portion necessarily comprises the same material as the balloon member 12. Similarly, for the embodiments of FIGS. 5A, 5B of Solar et al., there are limitations imposed by the fact that the waist portion necessarily comprises the same material as the inner tube 61. Because catheters for use in such procedures as angioplasties must be of very small overall diameter, there is an extremely limited range of acceptable sidewall thicknesses. Therefore, having to rely on differences in sidewall thickness, or on a limited range of materials, in order to achieve a variable stiffness balloon catheter unduly restricts the design of these instruments.

These and other problems with and limitations of the prior art balloon catheters are overcome with the variable stiffness balloon catheters of this invention.

OBJECTS OF THE INVENTION

Accordingly, it is a general object of this invention to provide a balloon dilatation catheter apparatus having a shaft portion characterized by at least two different degrees of stiffness along its length.

A principal object of this invention is to provide a relatively inexpensive and adaptable design for a variable stiffness balloon dilatation catheter.

A further object of this invention is to provide a variable stiffness balloon dilatation catheter in which the several component parts may comprise the same or different materials in order to customize the apparatus to almost any set of performance criteria.

A specific object of this invention is to provide a balloon dilatation catheter apparatus having two or more discrete, substantially uniform zones of stiffness along the shaft portion.

Still another specific object of this invention is to provide a variable stiffness balloon dilatation catheter apparatus comprising a shaft portion having a generally concentric, coaxial configuration of inner and outer hollow tubular members in which the outer surface of the outer tubular member and the inner surface of the inner tubular member may comprise lubricous, low-friction materials.

These and other objects and advantages of this invention will be better understood from the following description, which is to be read together with the accompanying drawings.

SUMMARY OF THE INVENTION

The variable stiffness balloon dilatation catheter apparatus of the present invention comprises a generally concentric, coaxial configuration of inner and outer hollow tubular members arranged so as to create an annular lumen between the inner and outer members, which lumen is in fluid communication with the inflatable interior of a balloon element. The balloon element is sealed at one end to the outer tubular member and, at the other end, to the inner tubular member so as to create a closed-ended balloon interior, all in generally conventional fashion. Variable stiffness along the shaft portion of the catheter is provided by one or more heat-shrunk polymeric sleeves which surround sections of the inner tubular member and serve as stiffening or reinforcement bands to create distinct regions having different degrees of stiffness.

BRIEF DESCRIPTION OF THE DRAWINGS

FIG. 1 is a schematic longitudinal sectional view of a variable stiffness balloon dilatation catheter according to one embodiment of the invention.

FIG. 2 is a schematic longitudinal sectional view of a variable stiffness balloon dilatation catheter according to another embodiment of this invention.

DETAILED DESCRIPTION OF THE INVENTION

Figure 3:
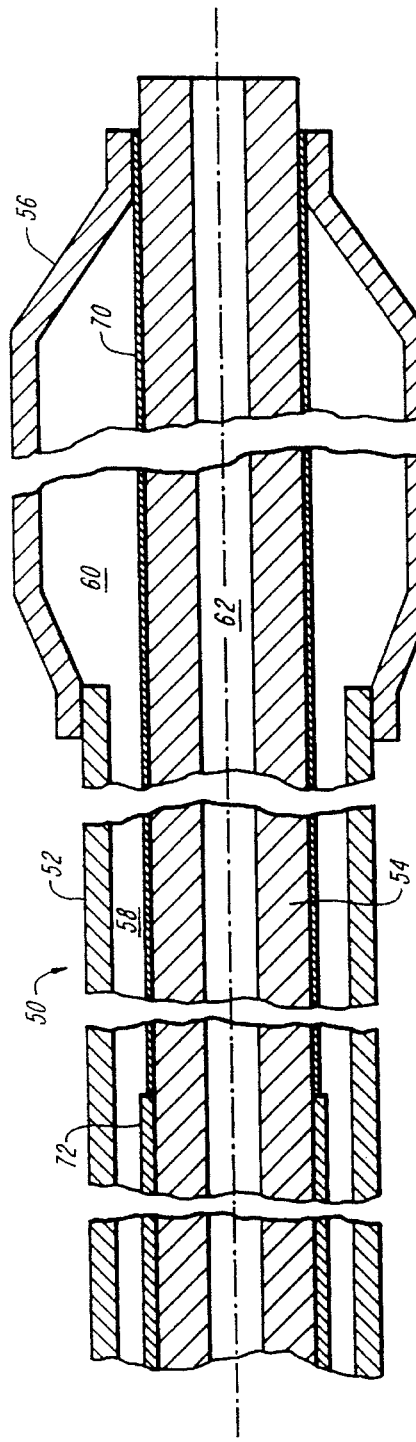
FIG. 3 is a schematic longitudinal sectional view of a variable stiffness balloon dilatation catheter according to yet another embodiment of the invention.

In each of the drawings, as described below, it should be understood that the wall thicknesses of the heat-shrunk polymeric sleeves relative to the inner and outer tubular members and to the balloon element, as well as relative to the overall dimensions of other elements, have generally been exaggerated for purposes of illustration.

FIG. 1 shows a schematic longitudinal sectional view of a variable stiffness balloon dilatation catheter 10 according to the present invention comprising a shaft portion having a generally concentric, coaxial configuration of an outer tubular member 12 and inner tubular member 14, and an inflatable balloon element 16 at or near the distal end of the shaft portion of the catheter. As seen in FIG. 1, the proximal end of balloon element 16 comprises a tapered portion adapted to be sealed to the distal end of outer tubular member 12. Correspondingly, the distal end of balloon element 16 comprises a tapered portion adapted to be sealed to the outside of inner tubular member 14.

Inner and outer tubular members 14 and 12 respectively are sized such that member 14 fits inside the hollow interior of member 12 creating a generally annular lumen 18 defined by the outer sidewall of member 14 and the inner surface of the sidewall of member 12. Annular lumen 18 is in fluid communication with the otherwise closed interior 20 of balloon element 16. Lumen 18 must be of sufficiently large cross-sectional area such that fluid from an external source can be supplied to balloon interior 20 in order to inflate balloon element 16, and subsequently withdrawn from balloon interior 20 in order to deflate balloon element 16, within a relatively short time period.

In general, inner tubular member 14, outer tubular 12, and balloon element 16 may comprise the same or different polymeric materials. The choice of materials will be dictated in part by the anticipated application and operating conditions for the catheter. It will be apparent, for example, that a balloon dilatation catheter intended for use in very narrow body passageways, such as blood vessels, will have a different and typically more demanding set of performance criteria than for an apparatus designed for use in a larger cavity. Thus, for a catheter device intended for a coronary angioplasty procedure, it is generally preferred that the balloon element have the properties of being extremely thin, high-strength, relatively inelastic, and readily inflatable under fluid pressure and readily collapsible under vacuum. But, if the "waist" portion of the catheter must be fabricated from the same material as the balloon element, as taught by FIGS. 2A, 2B, 4A, 4B, and 6A, 6B of Solar et al., it may not be possible to achieve the desired degree of stiffness for this catheter section given the inherent limitations on wall thickness in order to maintain the small overall catheter diameter.

For most conventional applications, inner tubular member 14 comprises at least one interior, generally centrally-located longitudinal channel or lumen 22 running the length of member 14. Lumen 22 is sized to fit over a previously positioned guide wire (not shown) to assist in threading the balloon catheter through a body passageway in order to site the balloon at a pre-determined internal location. Because the overall outside diameter of the catheter must be kept very small for such applications as PTCA catheters, lumen 22 is typically not much larger in diameter than the guide wire. Therefore, it is highly desirable to minimize the friction between the guide wire and the inner wall of member 14 (i.e. the tubular surface that defines lumen 22). This result can be accomplished, for example, by preparing inner tubular member 14 from a polymeric material that has the properties of being lubricous and having a very low coefficient of friction. Such materials include, by way of example, high density polyethylene (HDPE), particularly high molecular weight HDPE; fluoropolymers, particularly polytetrafluoroethylene (PTFE) polymers such as Teflon and Teflon-like compounds; polypropylene; nylon and nylon elastomers; and polyester elastomers.

For optimum catheter results, outer tubular member 12 should meet other performance criteria. Just as the inner wall of member 14 should comprise a low-friction surface to facilitate sliding over a guide wire, so too should the outer wall of member 12 be lubricous and have a low coefficient of friction to facilitate sliding the catheter through a narrow and tortuous body passageway with minimal trauma to surrounding tissue. At the same time, the sidewall of member 12 must be made of a sufficiently high-strength material to resist rupture or significant distortion under internal fluid pressure when balloon element 16 is being inflated. Such materials include, by way of example, high density polyethylene (HDPE), particularly high molecular weight HDPE; fluoropolymers, particularly polytetrafluoroethylene (PTFE) polymers such as Teflon and Teflon-like compounds; polypropylene; nylon and nylon elastomers; and polyester elastomers.

Correspondingly, the sidewall of member 14 should generally be sufficiently thick to resist collapse from internal fluid pressure in annular lumen 18 when the balloon is being inflated. This criterion severely limits the utility of a prior art configuration such as that shown in FIGS. 5A, 5B of the Solar et al. patent, where the thinner-walled waist portion of inner tube 61 would have a tendency to collapse during use if the wall was made too thin along this section in order to increase flexibility. Whereas the Solar et al. variable stiffness constructions rely on significant changes in the thickness of the sidewalls of the inner and outer tubular members, or on a balloon element made of a relatively low-stiffness, flexible material, to achieve variations in catheter stiffness, the present invention relies instead on a set of heat-shrunk polymeric stiffening bands. The advantages of this technique as compared with the prior art include the fact that it does not restrict the choice of materials for the inner and outer tubular members or the balloon element, and it results in little or no change in the inside diameter of the inner tubular member or in the overall diameter of the catheter.

As seen in FIG. 1, a first polymeric sleeve is heat-shrank directly over the outer surface of inner tubular member 14 to create a first stiffening band 30. As shown in FIG. 1, band 30 runs substantially from the proximal end of member 14 to the point where the distal end of balloon element 16 is sealed to member 14. The special advantages of this embodiment will be discussed hereinafter. Alternatively, for some applications, it may be desirable for band 30 to extend all the way to the distal end of member 14. FIG. 2 is substantially identical to FIG. 1 (and is correspondingly numbered except for the reference numerals identifying the overall catheter and the first stiffening band), with the difference that in FIG. 2 the catheter 40 comprises a shorter first polymeric sleeve heat-shrunk directly over the outer surface of inner tubular member 14 to create a first stiffening band 42 that terminates at a point prior to the distal end of member 12 and prior also to the proximal end of balloon element 16.

FIG. 1 further shows a second polymeric sleeve heat-shrunk over a portion of the outer surface of band 30 to form a second stiffening band 32 that runs substantially from the proximal end of member 14 to a point that is proximal of the distal end of member 12 and also proximal of the proximal end of balloon element 16. Furthermore, a third polymeric sleeve is heat-shrunk over a portion of the outer surface of band 32 to form a third stiffening band 34 that runs substantially from the proximal end of member 14 to a point that is proximal of the distal end of band 32. The configuration illustrated in FIG. 1 thus comprises a catheter having: a first degree of stiffness along that portion of the catheter where member 14 is surrounded only by band 30; a second degree of stiffness along that portion of the catheter where member 14 is surrounded by both bands 30 and 32; a third degree of stiffness along that portion of the catheter where member 14 is surrounded by bands 30, 32 and 34; and, a fourth zone of stiffness at the tip end of the catheter distal of the balloon. For some applications, such a soft-tipped catheter is desirable.

The polymeric sleeves that comprise bands 30, 32 and 34 may be fabricated from the same or different heat-shrinkable polymeric materials, and may be of the same or different thicknesses. The starting polymeric sleeves should be hollow, open-ended, thin-walled tubes having an interior diameter somewhat larger than the outer diameter of the member over which the sleeve is to be heat-shrunk. Suitable heat-shrinkable polymeric materials include polyethylene terephthalate (PET), nylon, polyethylenes, polyurethanes, fluoropolymers, polyesters, and polyimides. The polymeric sleeves should also comprise a material that has a flexural modulus greater than, preferably significantly such as about two to ten times greater than, that of the material comprising the tubular member.

A preferred material for the heat-shrinkable polymeric sleeves of this invention is polyethylene terephthalate (PET). The term "polyethylene terephthalate" or PET as used herein is intended to be used in a broad sense in that it generally refers to resins and products thereof in which the major proportion of the polymer is PET. To this end, the PET may be homopolymeric, or a copolymer. Typical examples of other suitable aromatic dicarboxylic acid polymers utilize materials such as terepthalic acid, isothalic acid, napthalene dicarboxylic acid, together with aliphatic polymethylene glycols having two to ten carbon atoms. Among these are ethylene glycol, trimethylene glycol, tetramethylene glycol, pentamethylene glycol, hexamethylene glycol, didecamethylene glycol and cyclohexane dimethanol. In addition to homopolymers and copolymers, other polymers or non polymeric materials may be melt blended or mixed together. It has been found that even a very thin PET sleeve surrounding a section of a polymeric tubular member can dramatically and unexpectedly increase the stiffness of that section of the tubular member while adding very little overall thickness to the tubular member. The PET sleeve may be uniaxially or biaxially oriented to provide even greater increases in stiffness for a given sleeve wall thickness.

Processes for heat-shrinking thin films of polymeric materials are generally well known in the art. With respect to PET sleeves, it has been found that shrinkage is a function of temperature: in general, the higher the temperature the greater the shrinkage. Shrinking temperatures typically range from about 85° C. (185° F.) to about 190° C. (374° F.), preferably about 120°–180° C. If a PET heat-shrink tube is unconstrained, it will shrink both radially and axially, but the presence of an inner tubular member will limit radial shrinkage. In most cases, the best overall performance is achieved with shrinkage of about 15–20% or less. Selection of starting tubing size, shrinkage temperature, and other process parameters for a particular polymeric material is a matter of routine experimentation.

In general, the starting polymeric sleeves for this invention will have wall thicknesses on the order of about 0.0001 to 0.003 inches, preferably about 0.0002 to 0.0015 inches, resulting in stiffening bands after heat shrinking having wall thicknesses about 10–20% greater, i.e. on the order of about 0.00012 to 0.0035 inches. In the preferred embodiment of this invention, the final wall thickness of the stiffening bands after heat shrinking will be such that the ratio of the band thickness to the outside diameter of the tubular member is about 1:5 or less, preferably about 1:10 or less along relatively stiffer sections and 1:30 or less along less-stiff sections. It will be apparent that the polymeric stiffening bands of this invention do not directly affect the overall outside diameter of the catheter because the polymeric sleeves are heat-shrunk around the inner tubular member 14. Nevertheless, it is important that the stiffening bands add relatively little diameter to the inner tubular member because, as seen in FIG. 1, they may partially block lumen 18 thereby impeding the flow of fluid to and from balloon interior 20.

In an alternative embodiment of this invention, however, any blockage of lumen 18 can be minimized or eliminated by utilizing a reduced wall thickness along portions of inner tubular member 14. In this alternative embodiment, instead of an inner member of substantially constant wall thickness as seen in FIG. 1, an inner member of varying wall thickness (comparable to inner tube 61 in FIGS. 5A, 5B of the Solar et al. patent) could be substituted. After heat-shrinking polymeric sleeves around the reduced wall thickness portions of the inner member to form stiffening bands in accordance with this invention, the inner member could be made to have a substantially constant overall diameter along its length while still imparting variable stiffness properties to the catheter. Indeed, in this alternative embodiment, stiffened portions of the inner member could be made with wall thicknesses and/or overall diameters less than unstiffened portions of the inner member. It will be apparent that the present invention create almost unlimited opportunities to custom design a balloon dilatation catheter to meet a wide range of performance requirements, a flexibility that does not exist with any of the prior art techniques.

In addition to obtaining four different stiffness regions along catheter 10 of FIG. 1, the embodiment of FIG. 1 has still another unexpected advantage. As noted above, it may be advantageous to fabricate inner member 14 from a highly lubricous polymer such as Teflon to minimize friction between the guide wire and the wall of lumen 22. In the past, however, it has proven difficult if not impossible to securely seal the distal end of balloon element 16 to an inner tubular member of Teflon or a Teflon-like material. But, by heat-shrinking a polymeric sleeve around member 14 to form a stiffening band 30 of a different, less-lubricous, more readily bondable polymeric material, the past problems of sealing the distal end of balloon element 16 can be largely overcome. Because band 30 surrounds the outside of inner tubular member 14, no catheter surface requiring a very low coefficient of friction is affected by the practice of this invention. Inner and outer tubular members 14 and 12 respectively may comprise any desirable lubricous polymers, while still obtaining the desired variable stiffness properties for the catheter as well as obtaining a more secure bond between the balloon and inner tubular member 14.

As previously discussed, FIG. 2 is substantially identical to FIG. 1 except that variable stiffness catheter 40 has a first polymeric sleeve heat-shrunk directly over the outer surface of inner tubular member 14 to create a first stiffening band 42 that terminates prior to the distal end of member 12 or the proximal end of balloon 16. It will be apparent that, in this embodiment of the invention, the distal end of balloon 16 must be sealed directly to the outer surface of member 14, which may be difficult if member 14 is made of Teflon or a Teflon-like material. On the other hand, the embodiment of FIG. 2 will be seen to create a catheter having a longer region of intermediate stiffness. Whereas FIGS. 1 and 2 illustrate embodiments of the invention utilizing three substantially overlapping stiffening bands to create four variable stiffness regions along the catheter, it will be apparent to those skilled in the art that fewer or greater numbers of overlapping stiffening bands may be formed in similar fashion in order to create fewer or more stiffness zones as desired. A single band heat-shrunk around a portion of member 14 will thus create at least two regions of different stiffness.

Figure 4:
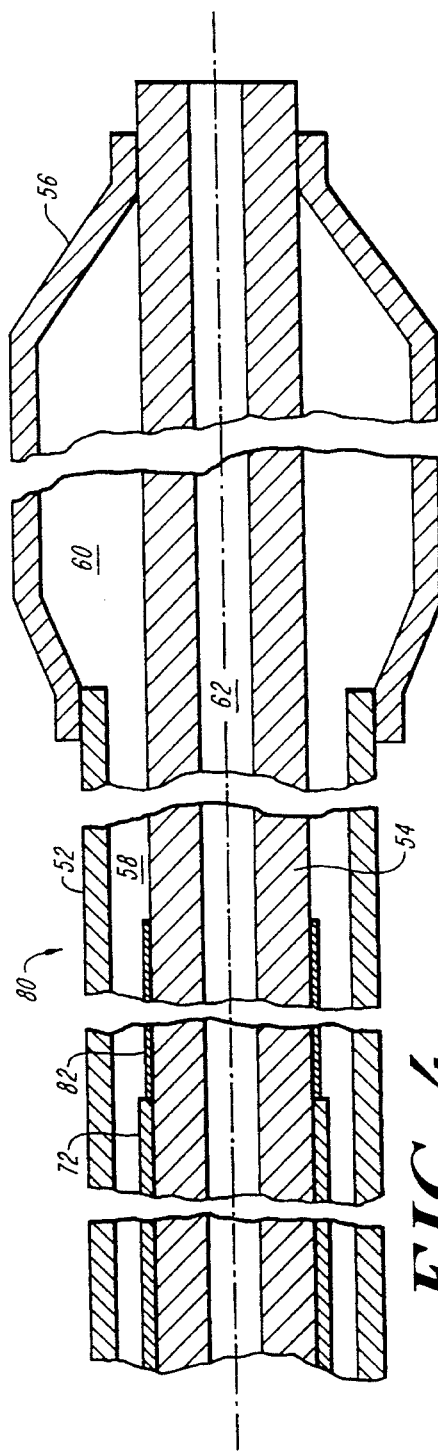
FIG. 4 is a schematic longitudinal sectional view of a variable stiffness balloon dilatation catheter according to still another embodiment of the invention.

FIGS. 3 and 4 illustrate alternative embodiments of this invention which do not utilize the overlapping stiffening bands of FIGS. 1 and 2. In FIG. 3, dilatation catheter 50 according to the present invention comprises a shaft portion having a generally concentric, coaxial configuration of an outer tubular member 52 and inner tubular member 54, and an inflatable balloon element 56 at or near the distal end of the shaft portion of the catheter. Inner and outer tubular members 54 and 52 respectively are sized such that member 54 fits inside the hollow interior of member 52 creating a generally annular lumen 58. Annular lumen 58 is in fluid communication with the otherwise closed interior 60 of balloon element 56, all comparable to the general catheter construction described above for FIGS. 1 and 2.

As seen in FIG. 3, a first polymeric sleeve is heat-shrunk directly over a first portion of the outer surface of inner tubular member 54 to create a first stiffening band 70, that first portion beginning at a point intermediate of the proximal end of member 54 and the distal end of member 52 and extending substantially to the distal end of balloon element 56. Alternatively, for some applications, it may be desirable for band 70 to extend all the way to the distal end of member 54. A second polymeric sleeve is heat-shrunk directly over a second portion of the outer surface of inner tubular member 54 to create a second stiffening band 72, that second portion extending substantially from the proximal end of band 70 to substantially the proximal end of member 54. It is within the scope of this embodiment of this invention for the distal end of band 72 to slightly overlap the proximal end of band 70, or vice versa. The catheter configuration illustrated in FIG. 3 thus has a first degree of stiffness along the portion of the catheter where member 54 is surrounded by band 70, a second degree of stiffness along the portion of the catheter where member 54 is surrounded by band 72, and a third degree of stiffness at the tip end of the catheter distal of the balloon.

The polymeric sleeves that comprise bands 70 and 72 may be fabricated from the same or different heat-shrinkable polymeric materials, and may be of the same or different thicknesses. The preceding discussion relating to the choice of materials for polymeric sleeves 30, 32 and 34 with respect to FIG. 1, as well as parameters such as wall thicknesses and heatshrinking temperatures, applies with equal effect to sleeves 70 and 72 in FIG. 3. In particular, uniaxially or biaxially-oriented PET is a preferred material for sleeves 70 and 72 because of the large and unexpected increase in stiffness that can be realized with a relatively thin PET heat-shrunk band. If both of bands 70 and 72 comprise biaxially-oriented PET, for example, then bands 70 and 72 would obviously need to be of different thicknesses in order to obtain variable stiffness properties, as shown in FIG. 3.

On the other hand, if bands 70 and 72 comprise different materials each having a different flexural modulus, then variable stiffness along the catheter can be realized while maintaining a substantially uniform overall diameter for inner member 54. Alternatively, as discussed above with respect to FIG. 1, an inner tubular member having a reduced wall thickness along some portions thereof can be substituted for the member 54 with substantially constant wall thickness. In this manner, two PET bands of different wall thicknesses could be heat shrunk around the different wall portions of the inner tubular member so as to obtain variable stiffness while preserving a substantially uniform overall diameter along the inner tubular member.

Similar to the embodiment of FIG. 1, the embodiment of FIG. 3 permits the distal end of balloon element 56 to be sealed to the outer surface of band 70 instead of directly to member 54. This configuration can be especially advantageous where member 54 comprises Teflon or a Teflon-like material. FIG. 4 is substantially identical to FIG. 3, and is correspondingly numbered, except that variable stiffness catheter 80 has a first polymeric sleeve heat-shrunk directly over the outer surface of member 54 to create a first stiffening band 82 that terminates prior to the distal end of member 52 or the proximal end of balloon 56. It will be apparent that, in this embodiment of the invention, the distal end of balloon 56 must be sealed directly to the outer surface of member 54, which may be difficult if member 54 is made of Teflon or a Teflon-like material. On the other hand, the embodiment of FIG. 4 will be seen to create a catheter having a longer region of intermediate stiffness. Whereas FIGS. 3 and 4 illustrate embodiments of the invention utilizing two substantially adjacent stiffening bands to create three stiffness regions along the catheter, it will be apparent to those skilled in the art that fewer or additional substantially adjacent stiffening bands could be formed in similar fashion in order to create fewer or additional stiffness zones as desired. A single band heat-shrunk around a portion of member 54 will thus create at least two regions of different stiffness.

The following examples will illustrate specific embodiments of the present invention:

EXAMPLE I

A balloon dilatation catheter comparable to that shown in FIG. 4 was prepared. Inner tubular member 54 and outer tubular member 52 were fabricated from high density polyethylene, and balloon element 56 was made from biaxially oriented PET. Inner member 54 had a substantially uniform outer diameter of 0.025 inches and included a central guide wire lumen having a diameter of 0.017 inches. Outer member 52 had a substantially uniform outer diameter of 0.0455 inches and a sidewall thickness of 0.004 inches, the same as for inner member 54. Balloon element 56 had a wall thickness of 0.0004 inches along the center or "working" portion of the balloon.

A first PET sleeve having an initial thickness of 0.0005 inches was heat shrunk around a portion of member 54 to form stiffening band 82. A second PET sleeve having an initial thickness of 0.001 inches was heat shrunk around an adjacent portion of member 54 to form stiffening band 72. It was determined that the region of the catheter shaft represented by band 82 would have a stiffness about twice that of the unbanded region distal of band 82. It was further determined that the region of the catheter shaft represented by band 72 would have a stiffness about four times that of the unbanded region. This example demonstrates the surprisingly large increases in catheter stiffness that can be realized with relatively thin heat-shrunk stiffening bands in accordance with one embodiment of this invention.

EXAMPLE II

A balloon dilatation catheter comparable to that shown in FIG. 2 was prepared. The catheter parameters for the inner and outer tubular members and the balloon were substantially identical to those of the corresponding elements of the catheter of Example I as set forth above. For this Example, however, a first 0.00035 inch PET sleeve was heat shrunk around a portion of member 14 to form stiffening band 42; a second 0.00035 inch PET sleeve was heat shrunk around a portion of band 42 to form stiffening band 32; and a third 0.00035 inch PET sleeve was heat shrunk around a portion of band 32 to form stiffening band 34.

It was determined that the region of the catheter shaft represented only by band 42 would have a stiffness about twice that of the unbanded region distal of band 42. It was further determined that the region of the catheter shaft represented by overlapping bands 32 and 42 would have a stiffness about three times that of the unbanded region. It was further determined that the region of the catheter shaft represented by overlapping bands 34, 32 and 42 would have a stiffness about four times that of the unbanded region. This example confirms the surprisingly large increases in catheter stiffness that can be achieved with relatively thin heat-shrunk stiffening bands in accordance with an alternative embodiment of this invention.

Since certain changes may be made in the above-described apparatuses and processes without departing from the scope of the invention herein involved, it is intended that all matter contained in the above description shall be interpreted in an illustrative and not in a limiting sense.

I claim:

1. In a balloon dilatation catheter apparatus comprising generally concentric, coaxial, inner and outer polymeric tubular members, each having proximal and distal ends, and arranged so as to form an annular lumen therebetween in fluid communication with the interior of an inflatable balloon element sealed at its proximal end to said outer tubular member and at its distal end to said inner tubular member, the improvement comprising: at least one heat-shrunk stiffening band surrounding at least some portion of the exterior of said inner tubular member so as to form a tubular sidewall having a first thickness along a first portion of said inner tubular member and at least a second, larger thickness along a second portion, further wherein at least one of said stiffening bands has a wall thickness substantially less than the wall thickness of said inner tubular member and consists essentially of a heat-shrunk polymeric material having a flexural modulus sufficiently greater than that of said inner tubular member such that the portion of said sidewall associated with said stiffening band has a flexural modulus substantially greater than that of said inner tubular member.

2. Apparatus according to claim 1 wherein said first portion of said inner tubular member begins at the distal end of said second portion and extends substantially to the distal end of said inner tubular member.

3. Apparatus according to claim 1 wherein said first portion of said inner tubular member begins at the distal end of said second portion and extends substantially to the distal end of said balloon element.

4. Apparatus according to claim 1 wherein said first portion of said inner tubular member begins at the distal end of said second portion and terminates before the proximal end of said balloon element.

5. Apparatus according to claim 1 wherein said first portion of said inner tubular member begins at the distal end of said second portion and terminates before the distal end of said outer tubular member.

6. Apparatus according to claim 1 further wherein said inner tubular member comprises at least an interior longitudinal lumen that runs the length of said inner tubular member.

7. Apparatus according to claim 1 wherein said inner tubular member comprises a first stiffening band heat-shrunk around said first and second portions of said inner tubular member, and a second stiffening band heat-shrunk around said first stiffening band along said second portion.

8. Apparatus according to claim 7 wherein said first stiffening band extends substantially to the distal end of said inner tubular member.

9. Apparatus according to claim 7 wherein said first stiffening band extends substantially to the distal end of said balloon element.

10. Apparatus according to claim 7 wherein said stiffening band terminates before the proximal end of said balloon element.

11. Apparatus according to claim 7 wherein said first stiffening band terminates before the distal end of said outer tubular member.

12. Apparatus according to claim 1 further wherein said inner tubular member comprises a third portion located proximally of said second portion and having a composite sidewall of a third thickness, said third thickness being larger than said second thickness.

13. Apparatus according to claim 12 wherein said inner tubular member comprises:

a first stiffening band heat-shrunk around said first, second and third portions of said inner tubular member; a second stiffening band heat-shrunk around said first stiffening band along said second and third portions; and, a third stiffening band heat-shrunk around said second stiffening band along said third portion.

14. Apparatus according to claim 13 wherein said first stiffening band extends substantially to the distal end of said inner tubular member.

15. Apparatus according to claim 13 wherein said first stiffening band extends substantially to the distal end of said balloon element.

16. Apparatus according to claim 13 wherein said first stiffening band terminates before the proximal end of said balloon element.

17. Apparatus according to claim 13 wherein said first stiffening band terminates before the distal end of said outer tubular member.

18. Apparatus according to claim 13 wherein said first, second and third stiffening bands consists essentially of the same material.

19. Apparatus according to claim 13 wherein at least two of said first, second and third stiffening bands consist essentially of different materials.

20. Apparatus according to claim 13 wherein said three stiffening bands consist essentially of different materials.

21. Apparatus according to claim 1 wherein said inner tubular member comprises a first stiffening band heat-shrunk around said first portion of said inner tubular member, and a second stiffening band, of larger thickness than said first stiffening band, heat-shrunk around said second portion.

22. Apparatus according to claim 21 wherein the proximal end of said first portion is substantially adjacent the distal end of said second portion.

23. Apparatus according to claim 22 wherein said first stiffening band extends substantially to the distal end of said inner tubular member.

24. Apparatus according to claim 22 wherein said first stiffening band extends substantially to the distal end of said balloon element.

25. Apparatus according to claim 22 wherein said first stiffening band terminates before the proximal end of said balloon element.

26. Apparatus according to claim 22 wherein said first stiffening band terminates before the distal end of said outer tubular member.

27. Apparatus according to claim 1 wherein at least one of said stiffening bands consists essentially of polyethylene terephthalate.

28. Apparatus according to claim 27 wherein said polyethylene terephthalate has been oriented in at least one direction.

29. Apparatus according to claim 27 wherein said polyethylene terephthalate has been biaxially oriented.

30. Apparatus according to claim 1 wherein each of said stiffening bands consists essentially of polyethylene terephthalate.

31. Apparatus according to claim 1 wherein the ratio of the thickness of said stiffening bands to the outside diameter of said inner tubular member is about 1:5 or less.

32. Apparatus according to claim 1 wherein said inner tubular member consists essentially of a lubricous material that is not readily bondable to other polymeric materials.

33. Apparatus according to claim 1 wherein said inner tubular member consists essentially of a fluropolymer.

34. Apparatus according to claim 1 wherein each of said stiffening bands consists essentially of the same material.

35. Apparatus according to claim 1 wherein at least two of said stiffening bands consist essentially of different materials.

36. Apparatus according to claim 1 further wherein each of said stiffening bands has a wall thickness substantially less than the wall thickness of said inner tubular member and each portion of the sidewall associated with at least one of said stiffening bands has a flexural modulus at least about twice that of said inner tubular member.

37. Apparatus according to claim 1 further wherein each of said stiffening bands has a wall thickness less than about one-half the wall thickness of said inner tubular member.

38. Apparatus according to claim 1 further wherein each of said stiffening bands has a wall thickness less than about one-quarter the wall thickness of said inner tubular member.

39. Variable stiffness balloon dilatation catheter apparatus comprising: (a) hollow inner and outer polymeric tubular members having different diameters, each with proximal and distal ends, said members being arranged concentrically such that an annular lumen is formed therebetween; (b) a balloon element sealed at its proximal end to said outer tubular member and at its distal end to said inner tubular member so as to form a closed-ended, inflatable balloon interior in fluid communication with said annular lumen; and (c) said inner tubular member further comprising regions of differing degrees of stiffness formed by heat-shrinking at least one relatively thin polymeric sleeve around a portion of a relatively thicker tubular element comprising a polymer different from said polymeric sleeve, wherein said polymeric sleeves consist essentially of material having a flexural modulus sufficiently greater than that of said tubular element such that the regions associated respectively with said polymeric sleeves have a flexural modulus substantially greater than that of said tubular element.

40. Apparatus according to claim 39 wherein said regions comprise at least first and second regions, said second region being located proximally of said first region and having a greater degree of stiffness than said first region.

41. Apparatus according to claim 40 wherein said first region comprises a section of said inner tubular member having a first polymeric sleeve heat-shrunk around its exterior wall, and said second region comprises a section of said inner tubular member having a second polymeric sleeve heat-shrunk around its exterior wall.

42. Apparatus according to claim 41 wherein said inner tubular member has a substantially uniform wall thickness along its length and further wherein said second polymeric sleeve is thicker than said first polymeric sleeve.

43. Apparatus according to claim 41 wherein said second polymeric sleeve has a greater flexural modulus than said first polymeric sleeve.

44. Apparatus according to claim 41 wherein said first polymeric sleeve extends substantially to the distal end of said inner tubular member.

45. Apparatus according to claim 41 wherein said first polymeric sleeve extends substantially to the distal end of said balloon element.

46. Apparatus according to claim 41 wherein said first polymeric sleeve terminates before the proximal end of said balloon element.

47. Apparatus according to claim 41 wherein said first polymeric sleeve terminates before the distal end of said outer tubular member.

48. Apparatus according to claim 40 wherein a section of said inner tubular member comprises a first polymeric sleeve heat-shrunk around the exterior wall of the inner tubular member, and wherein said second region comprises a section of said inner tubular member having a second polymeric sleeve heat-shrunk around the exterior of said first polymeric sleeve along a portion thereof, and said first region comprises the section of inner tubular member surrounded only by said first polymeric sleeve.

49. Apparatus according to claim 48 wherein said first polymeric sleeve extends substantially to the distal end of said inner tubular member.

50. Apparatus according to claim 48 wherein said first polymeric sleeve extends substantially to the distal end of said balloon element.

51. Apparatus according to claim 48 wherein said first polymeric sleeve terminates before the proximal ends of said balloon element.

52. Apparatus according to claim 48 wherein said first polymeric sleeve terminates before the distal end of said outer tubular member.

53. Apparatus according to claim 39 wherein said regions comprise first, second and third regions, said second region being located proximally of said first region and having a greater degree of stiffness than said first region, and said third region being located proximally of said second region and having a greater degree of stiffness than said second region.

54. Apparatus according to claim 53 wherein a section of said inner tubular member comprises a first polymeric sleeve heat-shrunk around the exterior wall of the inner tubular member, further wherein a portion of said first polymeric sleeve has a second polymeric sleeve heat-shrunk around its exterior, and wherein said third region comprises a section of said inner tubular member having a third polymeric sleeve heat-shrunk around the exterior of said second polymeric sleeve along a portion thereof, said second region comprises the section of inner tubular member surrounded only by said first and second polymeric sleeves, and said first region comprises the section of inner tubular member surrounded only by said first polymeric sleeve.

55. Apparatus according to claim 54 wherein said first polymeric sleeve extends substantially to the distal end of said inner tubular member.

56. Apparatus according to claim 54 wherein said first polymeric sleeve extends substantially to the distal end of said balloon element.

57. Apparatus according to claim 54 wherein said first polymeric sleeve terminates before the proximal end of said balloon element.

58. Apparatus according to claim 54 wherein said first polymeric sleeve terminates before the distal end of said outer tubular member.

59. Apparatus according to claim 54 wherein said first, second and third polymeric sleeves consist essentially of the same material.

60. Apparatus according to claim 54 wherein at least two of said first, second and third polymeric sleeves consist essentially of different materials.

61. Apparatus according to claim 54 wherein said three polymeric sleeves consist essentially of different materials.

62. Apparatus according to claim 39 wherein at least one of said polymeric sleeves consists essentially of polyethylene terephthalate.

63. Apparatus according to claim 62 wherein said polyethylene terephthalate has been oriented in at least one direction.

64. Apparatus according to claim 62 wherein said polyethylene terephthalate has been biaxially oriented.

65. Apparatus according to claim 39 wherein each of said polymeric sleeves consists essentially of polyethylene terephthalate.

66. Apparatus according to claim 39 wherein the ratio of the thickness of said polymeric sleeves to the outside diameter of said inner tubular member is about 1:5 or less.

67. Apparatus according to claim 39 wherein said inner tubular member consists essentially of a lubricous material that is not readily bondable to other polymeric materials.

68. Apparatus according to claim 39 wherein said inner tubular member consists essentially of a fluropolymer.

69. Apparatus according to claim 39 wherein each of said polymeric sleeves consists essentially of the same material.

70. Apparatus according to claim 39 wherein at least two of said polymeric sleeves consist essentially of different materials.

71. Apparatus according to claim 39 further wherein each of said polymeric sleeves has a wall thickness less than about one-half the wall thickness of said tubular element.

72. Apparatus according to claim 39 further wherein each of said polymeric sleeves has a wall thickness less than about one-quarter the wall thickness of said tubular element.

73. Variable stiffness catheter member comprising elongated polymeric tubing having regions of differing degrees of stiffness formed by heat-shrinking at least one relatively thin polymeric sleeve around a portion of a relatively thicker tubular element comprising a polymer different from said polymeric sleeve, wherein said polymeric sleeves consist essentially of material having a flexural modulus sufficiently greater than that of said tubular element such that the regions associated respectively with said polymeric sleeves have a flexural modulus substantially greater than that of said tubular element.

74. Catheter member according to claim 73 wherein said regions comprise first, second and third regions, said second region having a greater degree of stiffness than said first region, and said third region having a greater degree of stiffness than said second region.

75. Catheter member according to claim 74 wherein a section of said member comprises a first polymeric sleeve heat-shrunk around the exterior wall of said tubing, further wherein a portion of said first polymeric sleeve has a second polymeric sleeve heat-shrunk around its exterior, and wherein said third region comprises a section of said member having a third polymeric sleeve heat-shrunk around the exterior of said second polymeric sleeve along a portion thereof, said second region comprises the section of said member surrounded only by said first and second polymeric sleeves, and said first region comprises the section of said member surrounded only by said first polymeric sleeve.

76. Catheter member according to claim 73 wherein said regions comprise at least first and second regions, said second region having a greater degree of stiffness than said first region.

77. Catheter member according to claim 76 wherein said first region comprises a section of tubing having a first polymeric sleeve heat-shrunk around its exterior wall, and said second region comprises a section of said tubing having a second polymeric sleeve heat-shrunk around its exterior wall.

78. Catheter member according to claim 77 wherein said tubing has a substantially uniform wall thickness along its length and further wherein said second polymeric sleeve is thicker than said first polymeric sleeve.

79. Catheter member according to claim 77 wherein said second polymeric sleeve has a greater flexural modulus than said first polymeric sleeve.

80. Catheter member according to claim 76 wherein a section of said member comprises a first polymeric sleeve heat-shrunk around the exterior wall of said tubing, and wherein said second region comprises a section of said member having a second polymeric sleeve heat-shrunk around the exterior of said first polymeric sleeve along a portion thereof, and said first region comprises the section of said member surrounded only by said first polymeric sleeve.

81. Catheter member according to claim 73 further wherein each of said polymeric sleeves has a wall thickness less than about one-half the wall thickness of said tubular element.

82. Catheter member according to claim 73 further wherein each of said polymeric sleeves has a wall thickness less than about one-quarter the wall thickness of said tubular element.

* * * * *

UNITED STATES PATENT AND TRADEMARK OFFICE
CERTIFICATE OF CORRECTION

PATENT NO. : 5,499,973
DATED : March 19, 1996
INVENTOR(S) : Mark A. Saab

It is certified that error appears in the above-indentified patent and that said Letters Patent is hereby corrected as shown below:

Col. 11, lines 12-13 - between the words "exterior" and "of" insert the word --wall--.

Col. 12, line 20 - change "consists" to --consist--.

Signed and Sealed this

Second Day of July, 1996

Attest:

BRUCE LEHMAN

Attesting Officer

Commissioner of Patents and Trademarks